(12) United States Patent
Machida et al.

(10) Patent No.: US 9,149,174 B2
(45) Date of Patent: Oct. 6, 2015

(54) TRANSMITTANCE ADJUSTING DEVICE, OBSERVATION APPARATUS AND OBSERVATION SYSTEM

(75) Inventors: Ryo Machida, Kouza-gun (JP); Takeshi Suga, Hino (JP); Masahiro Kawauchi, Fuchu (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 1110 days.

(21) Appl. No.: 12/931,450

(22) Filed: Jan. 31, 2011

(65) Prior Publication Data

US 2011/0288387 A1 Nov. 24, 2011

Related U.S. Application Data

(63) Continuation of application No. PCT/JP2010/061165, filed on Jun. 30, 2010.

(30) Foreign Application Priority Data

Jul. 23, 2009 (JP) .................................. 2009-172421

(51) Int. Cl.
*A61B 1/06* (2006.01)
*A61B 1/00* (2006.01)
*A61B 5/02* (2006.01)

(52) U.S. Cl.
CPC ........... *A61B 1/0646* (2013.01); *A61B 1/00186* (2013.01); *A61B 5/02007* (2013.01)

(58) Field of Classification Search
CPC .......................... A61B 1/00186; A61B 1/0646

USPC .......... 600/160, 178, 181, 476; 359/885, 893; 362/583
See application file for complete search history.

(56) References Cited

U.S. PATENT DOCUMENTS

| 6,110,106 A * | 8/2000 | MacKinnon et al. .......... 600/181 |
| 6,212,425 B1 | 4/2001 | Irion et al. |
| 6,960,165 B2 | 11/2005 | Ueno et al. |

(Continued)

FOREIGN PATENT DOCUMENTS

| EP | 1 258 220 | 11/2002 |
| EP | 1 258 221 | 11/2002 |

(Continued)

OTHER PUBLICATIONS

European Supplementary Search Report, dated Nov. 20, 2012, issued in corresponding European Patent Application No. 10802155.1.

*Primary Examiner* — John P Leubecker
(74) *Attorney, Agent, or Firm* — Kenyon & Kenyon LLP (57) ABSTRACT

Using a transmittance adjusting device decreasing a transmittance of at least from 460 nm to 500 nm, which is a wavelength range between a point of end of a first optical absorption peak of hemoglobin and a point of start of a second optical absorption peak of hemoglobin, to between 20% and 70% for illuminating light from an illuminating light supply section or reflected light from an object, during observation of the inside of a body cavity, enhanced display of vessels with color reproduction that has no difference from that in observation under visible light, enabling color reproduction similar to that in observation under visible light and further enhanced display of vessels.

8 Claims, 9 Drawing Sheets

(56) References Cited

U.S. PATENT DOCUMENTS

| | | |
|---|---|---|
| 7,172,553 B2 | 2/2007 | Ueno et al. |
| 8,547,425 B2 * | 10/2013 | Ishihara .......................... 348/77 |
| 2007/0213588 A1 | 9/2007 | Morishita et al. |
| 2009/0040781 A1 * | 2/2009 | Ito ................................ 362/554 |
| 2009/0141343 A1 * | 6/2009 | Leard ........................... 359/359 |
| 2009/0306478 A1 * | 12/2009 | Mizuyoshi ................... 600/178 |
| 2009/0312607 A1 * | 12/2009 | Sunagawa et al. ............ 600/160 |

FOREIGN PATENT DOCUMENTS

| | | |
|---|---|---|
| JP | 2002-095635 | 4/2002 |
| JP | 2002-336196 | 11/2002 |
| JP | 2003-093343 | 4/2003 |
| JP | 2003-102684 | 4/2003 |
| JP | 2006-261861 | 9/2006 |
| JP | 2007-289278 | 11/2007 |
| JP | 2008-061969 | 3/2008 |

* cited by examiner

TRANSMITTANCE ADJUSTING DEVICE, OBSERVATION APPARATUS AND OBSERVATION SYSTEM

CROSS REFERENCE TO RELATED APPLICATION

This application is a continuation application of PCT/JP2010/061165 filed on Jun. 30, 2010 and claims benefit of Japanese Application No. 2009-172421 filed in Japan on Jul. 23, 2009, the entire contents of which are incorporated herein by this reference.

BACKGROUND OF THE INVENTION

1. Field of the Invention

The present invention relates to a transmittance adjusting device, an observation apparatus and an observation system, which adjust light with specific wavelengths to enhance contrast for observation of an object in the inside of a body.

2. Description of the Related Art

Endoscope apparatuses enabling, e.g., inspection of the inside of an organ, identification or treatment of an affected site by means of insertion into a body cavity of a patient without dissection have widely been used.

For such endoscope apparatuses, while ones that display a color observation image of the inside of a subject on a monitor using white color illuminating light close to natural light for normal observation have generally been used, in recent years, endoscope systems enabling narrow band imaging (NBI) in which light with two specific wavelengths is irradiated have been disclosed for example, in Japanese Patent Application Laid-Open Publication No. 2007-289278, the endoscope systems enabling observation with improved contrast of, e.g., blood vessels near the superficial portion of the mucous membrane of the inner wall of a body cavity to easily determine an affected region.

In contrast to the endoscope system disclosed in Japanese Patent Application Laid-Open Publication No. 2007-289278, for example, Japanese Patent Application Laid-Open Publication No. 2003-93343 discloses a technique in which an endoscope apparatus is provided with a red-color component cut filter that eliminates components with wavelengths causing deterioration of contrast of, e.g., the mucous membrane and blood vessels in the inside of a body cavity (long wavelengths) to ensure minimization of red-color components in a color image, enabling enhanced display of contrast between the mucous membrane and the blood vessels, and the other tissues.

Furthermore, for example, Japanese Patent Application Laid-Open Publication No. 2003-102684 discloses a technique in which an electronic endoscope apparatus is provided with a wavelength calibration filter that cuts off light with wavelengths of red-color components as long as such cutoff does not impair the color image, suppressing occurrence of halation, because mucous membranes in a living body largely reflect such light with red-color components.

SUMMARY OF THE INVENTION

In a transmittance adjusting device according to an aspect of the present invention, a transmittance for a wavelength at a first optical absorption peak of hemoglobin is not 0%, a transmittance for a wavelength range of no less than 460 nm and no more than 500 nm is no less than 20% and no more than 70% relative to the transmittance for the wavelength at the first optical absorption peak of hemoglobin, and a transmittance for a wavelength range more than 500 nm is not 0%, for white illuminating light from an illuminating light supply section or reflected light from an object illuminated with the illuminating light.

An observation apparatus according an aspect of the present invention includes: an image pickup section for detecting reflected light from an object in a body, the object being illuminated with white illuminating light, to pick up an image of the object; and a transmittance adjusting section in which a transmittance for a wavelength at a first optical absorption peak of hemoglobin is not 0%, a transmittance for a wavelength range of no less than 460 nm and no more than 500 nm is no less than 20% and no more than 70% relative to the transmittance for the wavelength at the first optical absorption peak of hemoglobin, and a transmittance for a wavelength range more than 500 nm is not 0%, for the illuminating light or the reflected light.

An observation system according to an aspect of the present invention includes: an illuminating light supply section for supplying illuminating light having a specific wavelength range; an image pickup section for detecting reflected light from an object in a body, the object being illuminated with the illuminating light, to pick up an image of the object; and a transmittance adjusting section in which a transmittance for a wavelength at a first optical absorption peak of hemoglobin is not 0%, a transmittance for a wavelength range of no less than 460 nm and no more than 500 nm is no less than 20% and no more than 70% relative to the transmittance for the wavelength at the first optical absorption peak of hemoglobin, and a transmittance for a wavelength range more than 500 nm is not 0%, for the illuminating light or the reflected light.

An observation system according to another aspect of the present invention includes: an image pickup section for detecting reflected light from an object in a body, the object being illuminated with illuminating light, to pick up an image of the object; and a light source in which an average light intensity in a wavelength range of no less than 460 nm and no more than 500 nm is no less than 20% and no more than 70% relative to a maximum intensity except zero in a wavelength range of no less than 400 nm and no more than 450 nm, and an average light intensity in a wavelength range more than 500 nm is not zero.

The transmittance adjusting device, the observation apparatus and the observation system according to the respective inventions stated above enable reproduction of colors like that in observation under visible light, in in-vivo observation, and enabling provision of further enhanced display of blood vessels.

DETAILED DESCRIPTION OF THE PREFERRED EMBODIMENT(S)

Hereinafter, embodiments of the present invention will be described with reference to the drawings.

First Embodiment

First, a first embodiment of the present invention will be described.

Figure 1:
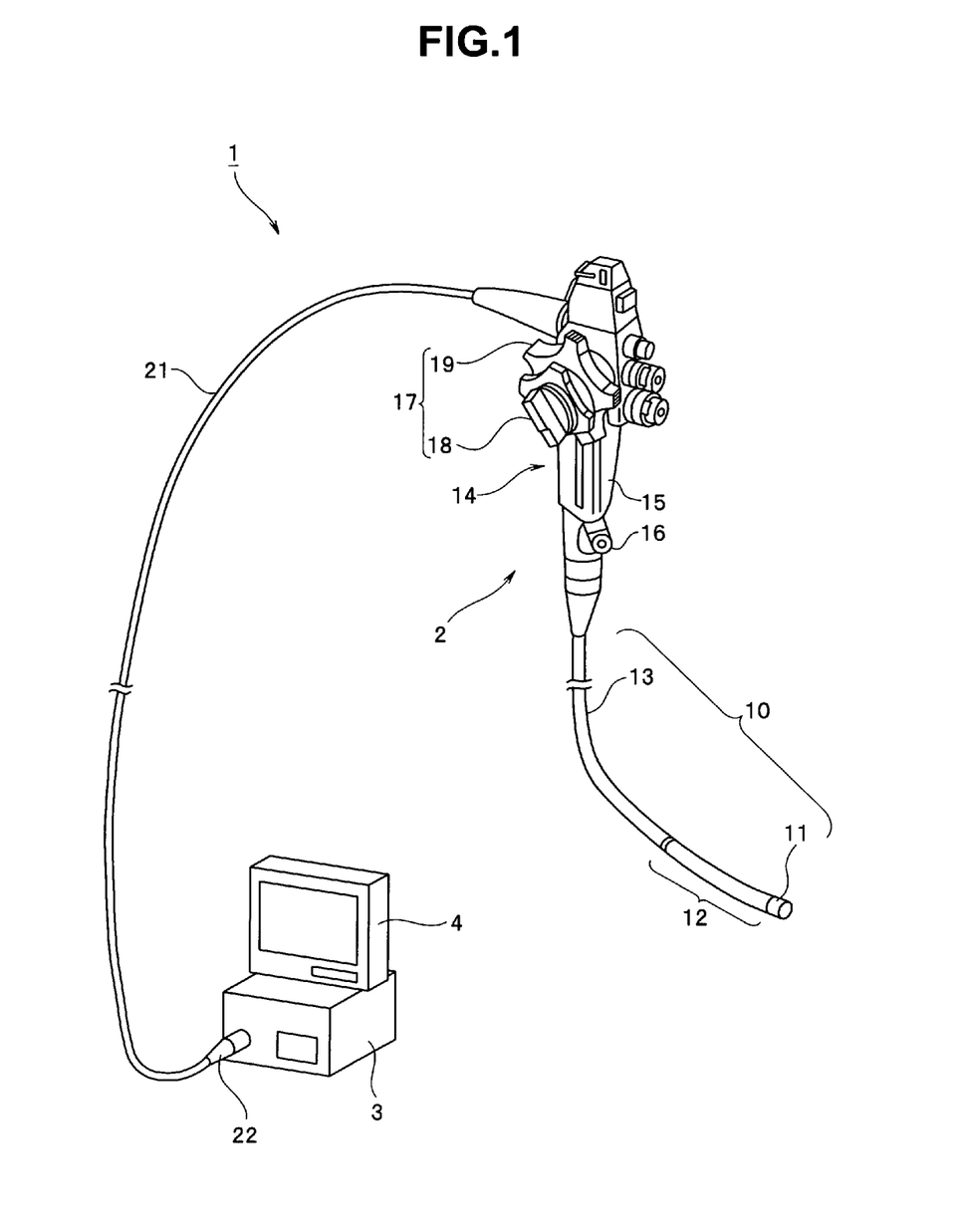
FIG. 1 is a perspective view illustrating an overall configuration of an observation system according to a first embodiment of the present invention.
Figure 2:
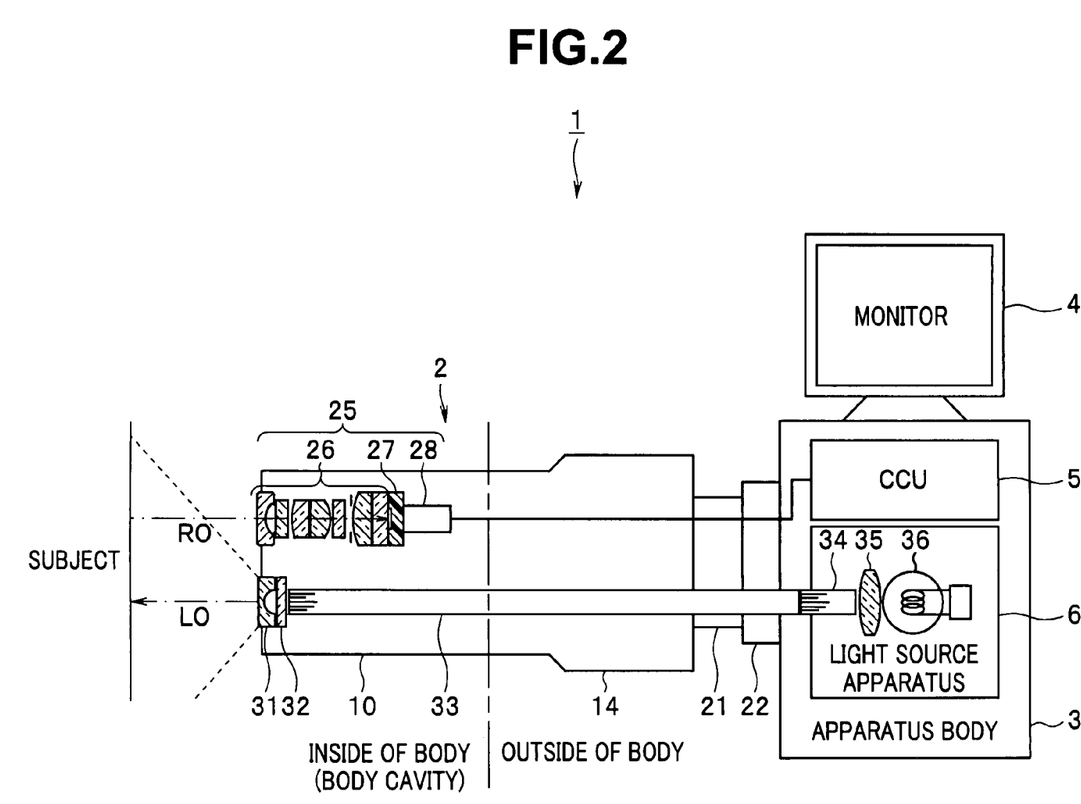
FIG. 2 is a block diagram illustrating a schematic configuration of the observation system according to the first embodiment of the present invention.
Figure 3:
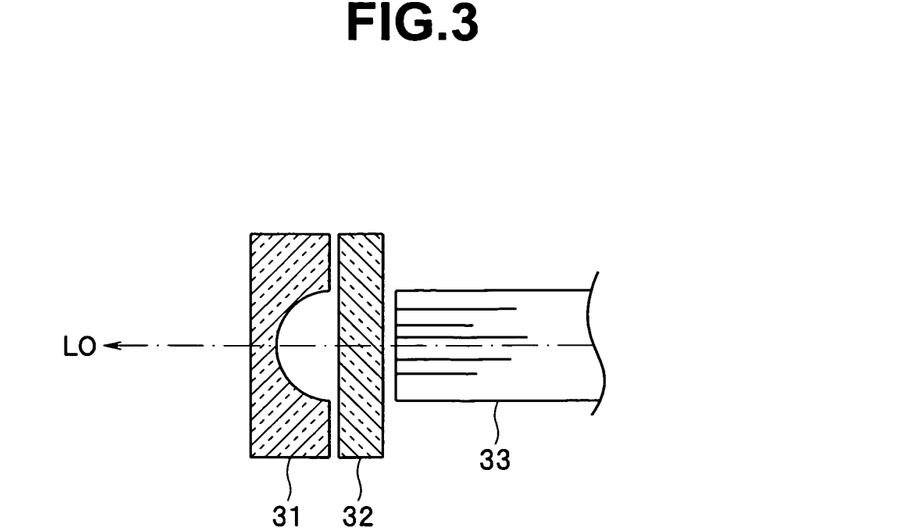
FIG. 3 is a diagram illustrating an arrangement of an illumination optical system disposed in an endoscope according to the first embodiment of the present invention.
Figure 4:
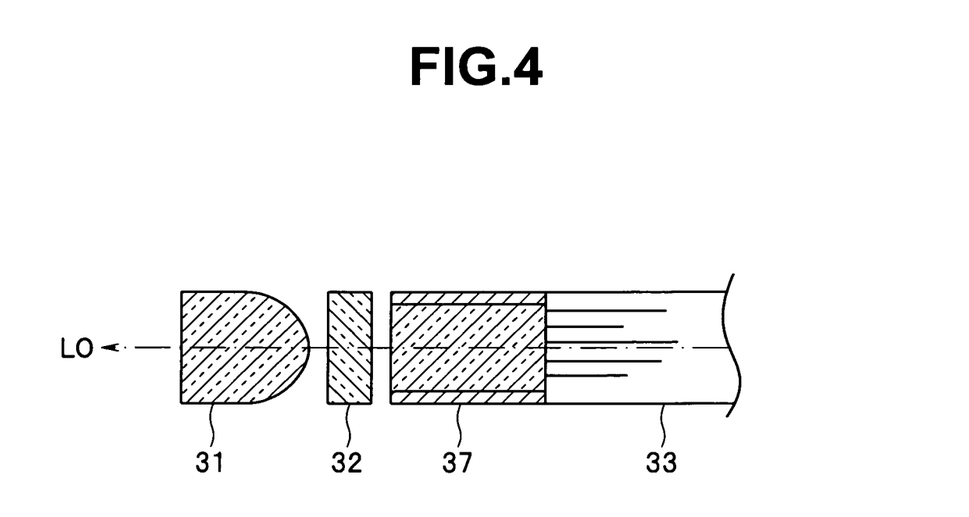
FIG. 4 is a diagram illustrating an arrangement of an illumination optical system disposed in an endoscope according to a variation of the first embodiment of the present invention.
Figure 5:
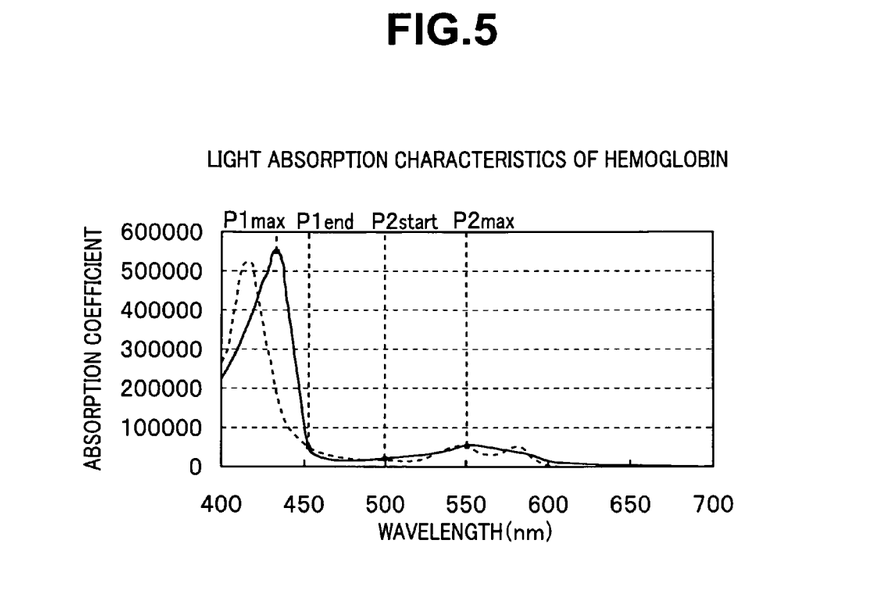
FIG. 5 is a graph indicating light absorption characteristics of hemoglobin according to the wavelength according to the first embodiment of the present invention.
Figure 6:
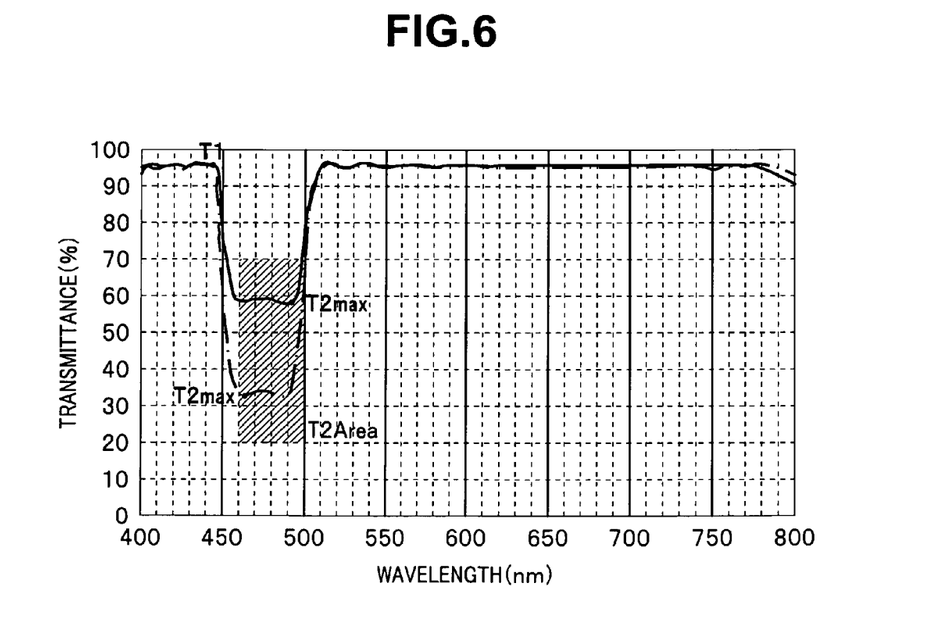
FIG. 6 is a graph indicating transmission characteristics of an optical filter relative to light wavelength according to the first embodiment of the present invention.
Figure 7:
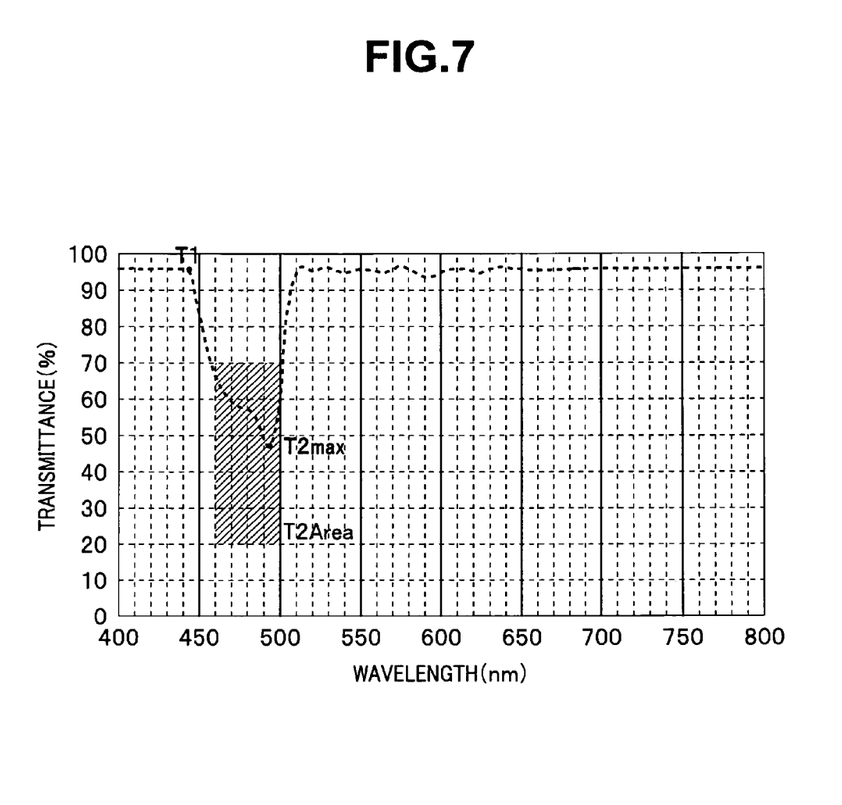
FIG. 7 is a graph indicating transmission characteristics of an optical filter relative to light wavelength according to a variation of the first embodiment of the present invention.
Figure 8:
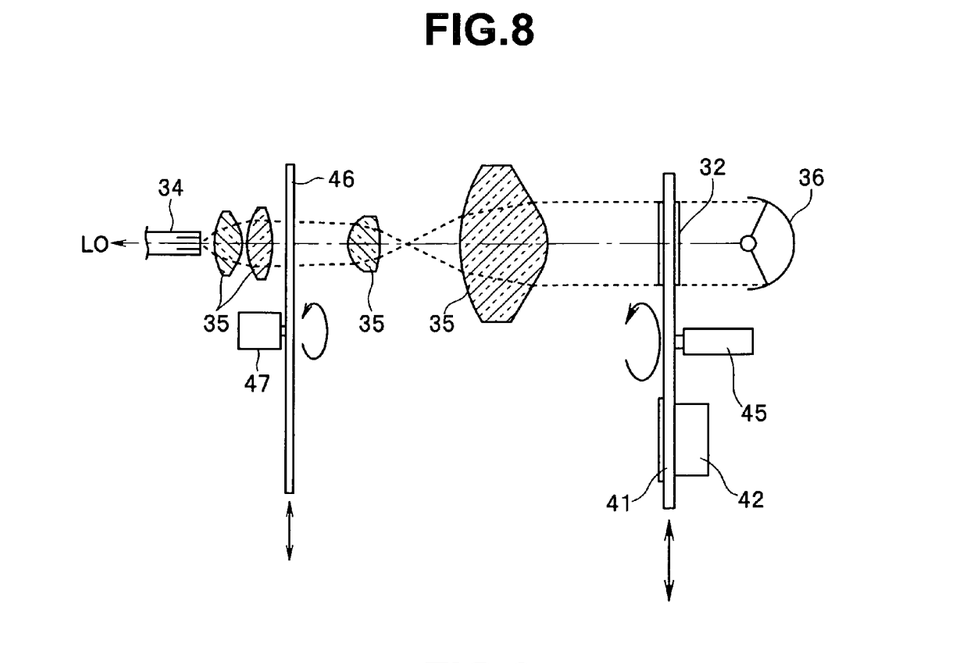
FIG. 8 illustrates a variation of the first embodiment, and is a diagram illustrating a configuration of the inside of a light source apparatus including a turret with an optical filter placed therein.
Figure 9:
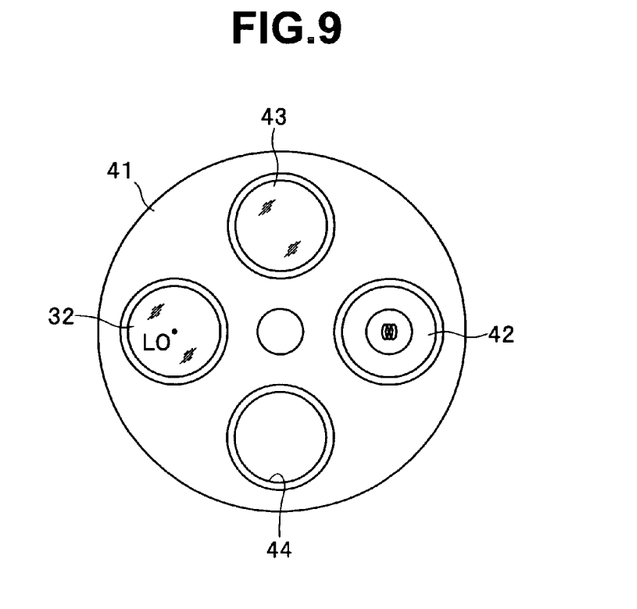
FIG. 9 is a plan view of the turret in FIG. 8 according to the variation of the first embodiment.

FIGS. 1 to 10 relate to the first embodiment of the present invention: FIG. 1 is a perspective view illustrating an overall configuration of an observation system; FIG. 2 is a block diagram illustrating a schematic configuration of the observation system; FIG. 3 is a diagram illustrating an arrangement of an illumination optical system disposed in an endoscope; FIG. 4 is a diagram illustrating an arrangement of an illumination optical system disposed in an endoscope according to a variation; FIG. 5 is a graph indicating light absorption characteristics of hemoglobin according to light wavelengths; FIG. 6 is a graph indicating transmission characteristics of an optical filter relative to light wavelengths; FIG. 7 is a graph indicating transmission characteristics of an optical filter relative to light wavelengths in a variation; FIG. 8 relates to a variation, and is a diagram illustrating a configuration of the inside of a light source apparatus including a turret with an optical filter placed therein; FIG. 9 is a plan view of the turret in FIG. 8; and FIG. 10 relates to a variation, and is a diagram illustrating a configuration of an image pickup unit in which an optical filter is placed in an objective lens group.

An endoscope system 1 illustrated in FIGS. 1 and 2, which is an observation system according to the present embodiment, mainly includes an endoscope 2, which is an observation apparatus, an apparatus body 3 with a camera control unit (CCU) 5 connected to the endoscope 2 and a light source apparatus 6 including illuminating light supply means integrally included therein, and a monitor 4 that display an endoscope image.

The endoscope 2, which is to be inserted into, e.g., a body cavity in the inside of a body, includes: an insertion portion 10, which is a narrow elongated member to be inserted into a site subject to in-vivo observation; an operation section 14 including a grasping portion 15 jointed to a proximal end portion of the insertion portion 10; a universal cable 21 extending from a side surface of the operation section 14; and a connector portion 22 provided at an end portion of the universal cable 21, the connector portion 22 being detachably connected to the apparatus body 3.

The insertion portion 10 includes a distal end portion 11 on the distal end side, and a bending portion 12 is provided following a rear portion of the distal end portion 11 as a bendable moving section. Furthermore, a flexible tube portion 13, which has a long length and flexibility and includes a flexible tube-shaped member, is jointed to a rear portion of the bending portion 12.

Also, in the operation section 14, e.g., a bending operation section 17, which includes a bending operation knob 19 in which two operation bodies for bending operation of the bending portion 12 are rotatably arranged in an overlapping manner and a fixing lever 18 for fixing the bending operation knob 19 at a desired rotational position, are disposed in a predetermined manner. Reference numeral 16 denotes a treatment instrument insertion opening, which is communicated with a proximal end of a treatment instrument channel (not illustrated) inserted in the insertion portion 10.

As illustrated in FIG. 2, the endoscope 2, which includes an image pickup unit 25 therein, the image pickup unit 25 being means for picking up an image of an object as well as an image pickup section, includes: an illumination lens 31 as an illuminating optical member; a light guide bundle 33, which is conveyance means for conveying illuminating light supplied from the light source apparatus 6 as well as a conveyance section; and an optical filter 32 provided between the illumination lens 31 and the light guide bundle 33.

The image pickup unit 25 includes: an objective lens group 26, which is an objective optical system including a plurality of lenses and optical components; a solid image pickup device 27, such as a CCD or CMOS, arranged behind the objective lens group 26; and an element circuit section 28 that performs photoelectric conversion of an image of image taking light collected by the objective lens group 26 and received by the solid image pickup device 27. The element circuit section 28 is electrically connected to the CCU 5 in a state in which the endoscope 2 is connected to the apparatus body 3, and outputs image signals resulting from the conversion to the CCU 5. The CCU 5 also performs video processing to make the input image signals be suitable for display on the monitor 4, and outputs video signals to the monitor 4.

As illustrated in FIG. 3, a plano-concave lens is here used for the illumination lens 31. In the present embodiment, the optical filter 32 arranged behind the illumination lens 31 forms a transmittance adjusting device, which is transmittance adjusting means as well as a transmittance adjusting section for decreasing a specific wavelength range of white color illuminating light conveyed by the light guide bundle 33 with a predetermined transmittance.

As illustrated in FIG. 4, the illumination lens 31 arranged at the front of the optical filter 32 may be a plano-convex lens. A single-fiber rod 37 for illumination unevenness decrease is placed between the optical filter 32 and the light guide bundle 33.

The light guide bundle 33 establishes a light conveyance path jointly with the light source apparatus 6 in a state in which the endoscope 2 is connected to the apparatus body 3. The light source apparatus 6 include known components such as an apparatus-side light guide bundle 34 connected to the light guide bundle 33 on the endoscope 2 side via a non-illustrated optical component, a lens 35 that collects illuminating light into the apparatus-side light guide bundle 34, and a light source 36, which is an illuminating light supply section (means) that emits illuminating light, such as a xenon lamp or a halogen lamp.

With the configuration as described above, in the endoscope system 1 according to the present embodiment, illuminating light indicated by an optical axis LO of an illuminating optical path, which have been conveyed from the light source apparatus 6, is reflected by an object, a part of the reflected light becomes image taking light indicated by an optical axis RO of an image taking optical path and is detected by the image pickup unit 25, and an endoscope image is displayed on the monitor 4 via the CCU 5.

Next, optical characteristics of the optical filter 32 according to the present embodiment will be described.

Transmittance characteristics with a specific wavelength range are set to the optical filter 32 according to the present embodiment based on the light absorption characteristics of hemoglobin in blood for a visible light ray (white color light) in a wavelength range of 400 nm to 700 nm.

As illustrated in FIG. 5, the light absorption characteristics of hemoglobin in blood for a visible light ray (white color light) can be indicated by curved lines each having two light absorption peaks P1max and P2max. Among the curved lines in FIG. 5, the curved line for oxygenated hemoglobin is indicated by a dashed line and the curved line for reduced hemoglobin is indicated by a solid line.

As can be seen from FIG. 5, light absorption peaks of hemoglobin (here, reduced hemoglobin) for a visible light ray exist in a wavelength range of around 445 nm to 450 nm, which is a first optical absorption peak P1max and at wavelengths of around 550 nm, which is a second optical absorption peak P2max. Light in the wavelength range of around 445 nm to around 450 nm at the first optical absorption peak P1max is light with blue colors close to purple. Light with the wavelengths of around 550 nm at the second optical absorption peak P2max is mainly light with colors ranging from green colors in a wavelength range of around 495 nm to around 570 nm to light with yellow colors on the longer wavelength side relative to the green colors.

The wavelength range between the first optical absorption peak P1max and the second optical absorption peak P2max corresponds to light with blue colors close to green, and after the second optical absorption peak P2max, the light becomes light with intensity of a red color more raised as the wavelength range becomes one for longer wavelengths.

Accordingly, hemoglobin has the characteristic of mainly absorbing light around the first optical absorption peak P1max and around the second optical absorption peak P2max, and reflecting light other than that at the first optical absorption peak P1max and the second optical absorption peak P2max, and accordingly visually produces red colors.

The light in the wavelength range of around 450 nm to around 500 nm is rarely absorbed by hemoglobin and thus, becomes reflected or scattered light, causing deterioration in vessel contrast, resulting in difficulty in observation.

Therefore, the optical filter 32 according to the present embodiment is configured so as to decrease the transmittance of light with wavelengths of around 450 nm, which causes deterioration in contrast of vessels to cell tissues in a body, here, as illustrated in FIG. 5, in a wavelength range of from 460 nm immediately after a point of end at which the first optical absorption peak P1max of hemoglobin completely ends (P1end) to 500 nm.

The effect of vessel contrast in a body being enhanced compared to the case where no optical filter 32 is provided, by providing a transmittance of no more than 70% for the entire area of a transmittance T2 of the optical filter 32 at least for a wavelength range of no less than 460 nm and no more than 500 nm, relative to a transmittance T1 of the optical filter 32 for the wavelength range of around 445 nm to around 450 nm has been verified.

Accordingly, as indicated by the solid line in FIG. 6, the optical filter 32 is set according to a roughly rectangular curve so as to provide a transmittance T1 of 95% for the wavelength range of around 445 nm to around 450 nm, which is the first optical absorption peak P1max of hemoglobin, while providing, for example, a maximum transmittance T2max of around 58% at least for the wavelength range of no less than 460 nm and no more than 500 nm. In other words, the transmittance T2 of the optical filter 32 has the light transmission characteristic of having a maximum relative transmittance of approximately 61% ($\approx$58%/95%) relative to the transmittance T1.

In such state, an endoscope image of an object in a body displayed on the monitor 4 of the endoscope system 1 had normal color reproduction comparable in any way to that in normal observation under visible light (white color light), and provided enhanced display of contrast of vessels to cell tissues in the body.

For color reproduction equivalent to that in normal observation with illuminating light under visible light (white color light), it is preferable to provide a light transmission characteristic of no less than 20% for the entire area of the transmittance T2 of the optical filter 32 at least for the wavelength range of no less than 460 nm and no more than 500 nm, relative to the transmittance T1 of the optical filter 32 for the wavelength range of around 445 nm to around 450 nm, which is the first optical absorption peak P1max of hemoglobin.

Meanwhile, it has been verified that where the optical filter 32 has the light transmission characteristic of the transmittance T2 being less than 20% relative to the transmittance T1, enhanced display of contrast of vessels to cell tissues in the body can be provided as an endoscope image in the endoscope system 1, but the endoscope image has color reproduction different from that in normal observation. Furthermore, it has also been verified that as with the endoscope 2 of the endoscope system 1 according to the present embodiment, in the case of the light transmission characteristic of the transmittance T2 being less than 20% relative to the transmittance T1, an effect, such as color noise caused by a gain at the time of white balance particular to electronic endoscopes which detect image taking light by means of the solid image pickup device 27 and convert the light into signals by means of an electronic circuit, is caused.

Accordingly, it has been verified that as indicated by the dashed-dotted line in FIG. 6, the optical filter 32 is set according to such a roughly rectangular curve as one providing a maximum transmittance T2max of, for example, around 34% at least for a wavelength range of no less than 460 nm and no more than 500 nm relative to the optical transmittance of 95% for the wavelengths at the first optical absorption peak P1max, the maximum relative light transmittance in the transmittance T2 relative to the transmittance T1 is approximately 36% ($\approx$34%/95%), and color reproduction similar to that in normal observation is provided in the endoscope system 1 and enhanced display of contrast of vessels to cell tissues in the body is also provided.

Consequently, the endoscope system 1 according to the present embodiment enables provision of color reproduction in an endoscope image similar to that in normal observation and enhanced display of contrast of vessels to cell tissues in a body as a result of the light transmission characteristics of the optical filter 32 being set so that the transmittance T2 for the wavelength range of no less than 460 nm and no more than 500 nm falls within a relative transmittance range of 20% to 70% (T2 Area indicated by the shaded lines in FIG. 6) relative to the transmittance T1 for the wavelength range of around 445 nm to around 450 nm, which is the first optical absorption peak P1max in the light absorption characteristics of hemoglobin.

Also, in the present embodiment, at least colors in a spectrum for the wavelength range of no less than 460 nm and no more than 500 nm in illuminating light, which is visible light (white color light) from the light source apparatus 6, are optically decreased by means of the optical filter 32, enabling enhancement of vessel expression without causing harm for image pickup (harmful light ray) such as halation.

The optical components of generated illuminating light vary depending on the type of the light source 36 such as a lamp, and the spectrum characteristics (spectrum distribution) of illuminating light (or light reflected by an object) is determined according to the optical transmittances of the light guide bundle 33 that conveys the illuminating light and the image pickup unit 25 including the objective lens group 26 and the solid image pickup device 27 that detect image taking light. Accordingly, the transmittance T2 for the wavelength range of no less than 460 nm and no more than 500 nm is not limited to that having the light transmission characteristics according to the roughly rectangular curve, and may be set so as to have light transmission characteristics according to, for example, a substantially unguiform curve as illustrated in FIG. 7 so as to decrease (cut off) light in the wavelength range of no less than 460 nm and no more than 500 nm to conform to the spectrum distribution calculated from the respective total spectrum characteristics of the illumination optical system and the image pickup optical system, and the transmittance characteristics.

With the light transmission characteristics according to the substantially unguiform curve conforming to the total spectrum distributions of the illumination optical system and the image pickup optical system, the transmittance T2 of the optical filter 32 for the wavelength range of no less than 460 nm and no more than 500 nm is set so as to fall within a relative transmittance range of 20% to 70% (T2Area indicated by the shaded line in FIG. 7) relative to the transmittance T1 for the wavelength range of around 445 nm to around 450 nm, which is the first optical absorption peak P1max in the light absorption characteristics of hemoglobin.

Consequently, the endoscope system 1 according to the present embodiment enables provision of color reproduction in in-vivo observation similar to observation under visible light (white color light) and enhanced display of vessels without causing, e.g., halation, which causes harmful light rays, by means of the light transmission characteristics of the optical filter 32 in which the spectrum for a specific wavelength range is decreased according to the light absorption characteristics of hemoglobin. Accordingly, the endoscope system 1 enables, in particular, effective and stable enhanced display of capillary vessels in the superficial portion of a mucous membrane. As described above, the endoscope system 1 enables enhanced display of contrast of vessels in a body even in an endoscope image, which is similar to that in observation under visible light, and thus, enhances expression of vessels, providing an advantage in that, for example, an affected site in which the amount of production of vessels increases can easily be determined.

Although the present embodiment has been described in details for the transmittance characteristics of the optical filter 32 based on reduced hemoglobin, it should be understood that a same operation and effect can be provided using oxygenated hemoglobin.

Also, the optical filter 32 may be arranged at any of positions on the optical path of illuminating light such as a position between illumination lenses, which are included in an (illumination) optical system for collecting light from the light source 36 in the light source apparatus 6, a position at an incident end of the light guide bundle 33 in the endoscope 2 and a position in the illumination optical system in the distal end portion 11 of the endoscope 2, or at any of positions on the optical path of image taking light such as a position in the objective optical system of the image pickup unit 25 and a position between the objective optical system and the solid image pickup device 27.

For example, as illustrated in FIGS. 8 and 9, the optical filter 32 may be provided in the turret 41 disposed in the light source apparatus 6.

The turret 41, which includes an emergency light unit 42, another optical filter 43 and an opening portion 44 formed in a circumferential direction, is rotated by a motor 45, thereby enabling the respective optical filters 32 and 43, the emergency light unit 42 and the opening portion 44 to be selectively arranged on the optical axis LO of illuminating light.

Furthermore, the light source 36 includes a turret 46 with an RGB filter placed therein, which is rotated by a motor 47. These turrets 41 and 46 also can be driven to advance and retract in a direction orthogonal to the optical axis LO of the illuminating light by means of a non-illustrated drive apparatus.

Figure 10:
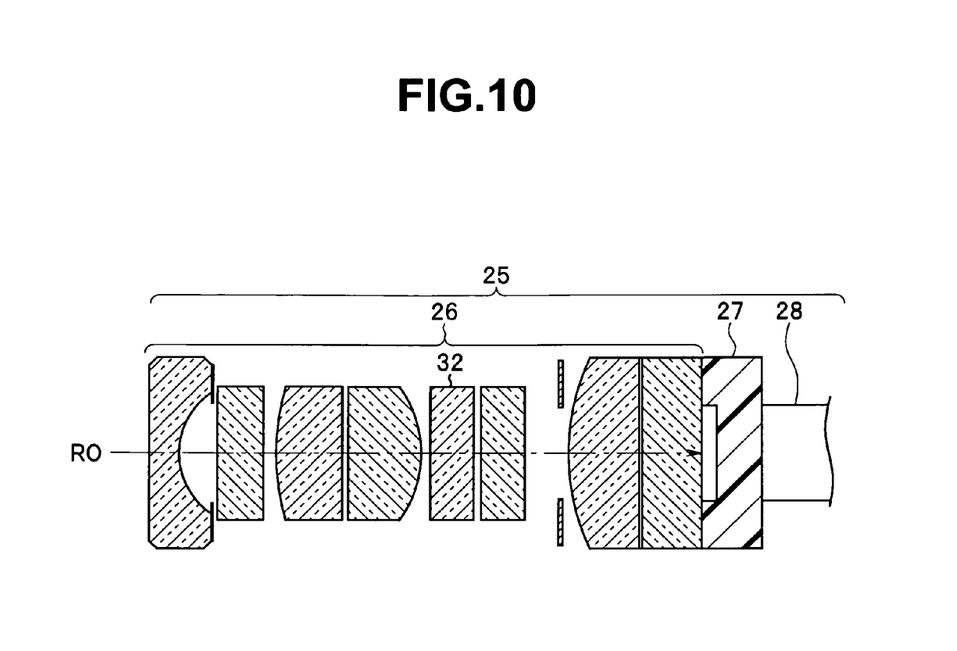
FIG. 10 illustrates a variation of the first embodiment, and is a diagram illustrating a configuration of an image pickup unit in which an optical filter is placed in an objective lens group.

Also, as illustrated in FIG. 10, the optical filter 32 may be arranged on the optical axis RO of image taking light as a part of the objective lens group 26.

Second Embodiment

Next, a second embodiment of the present invention will be described.

Figure 11:
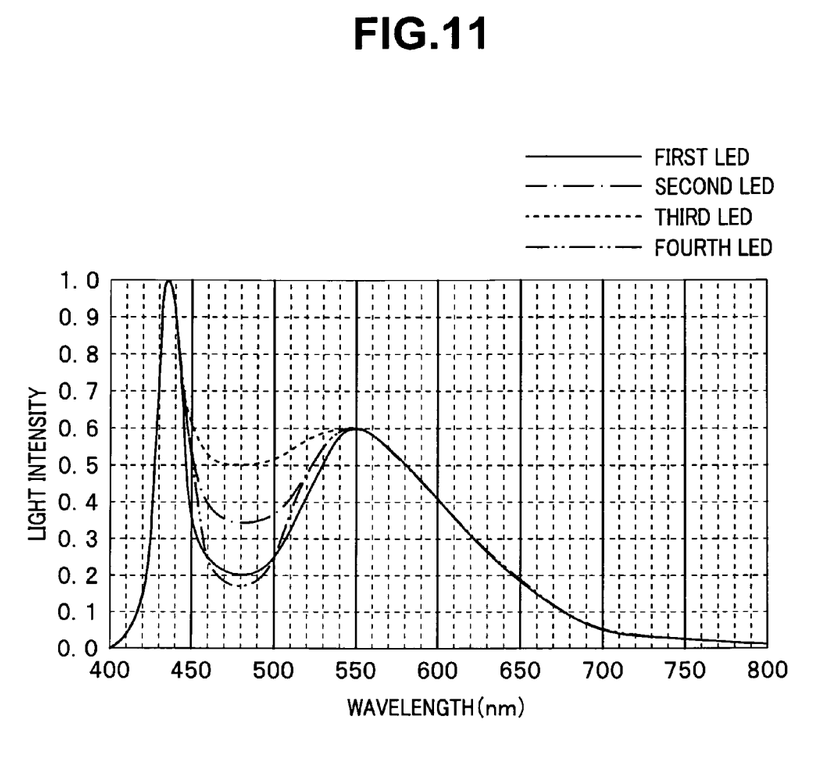
FIG. 11 relates to a second embodiment of the present invention, and is a graph indicating relative spectral characteristics of LEDs.

FIG. 11 relates to the second embodiment of the present invention and is a graph indicating relative spectrum characteristics of LEDs. In the present embodiment, components described in the first embodiment will be described using same reference numerals as those in the first embodiment.

It has been verified that a similar vessel contrast enhancement effect can be provided by decreasing light of around 450 nm to around 500 nm as a result of changing the spectrum characteristics of a light source itself in a light source apparatus 6 without using a transmittance adjusting device.

For example, where an LED is used for a light source disposed in the light source apparatus 6 or a distal end portion 11 of an insertion portion 10 of an endoscope 2, desired spectrum characteristics can be obtained by changing the characteristics of phosphors. A similar effect can also be provided by combination of a plurality of LEDs with different spectrum characteristics. In such a manner, as described in FIG. 11, for example, three light intensities of first to third LEDs are made to have a light intensity of no less than 20% and no more than 70% (in the Figure, a light intensity of no less than 0.2 and no more than 0.7) at least for a wavelength range of no less than 460 nm and no more than 500 nm relative to a maximum intensity (in the Figure, a light intensity of 1.0) in a wavelength range of no less than 400 nm and no more than 450 nm, enabling decrease of light in a wavelength range causing vessel contrast deterioration. With such configuration, an effect similar to that in the case where the transmittance adjusting device described in the above-described first embodiment is used can be provided.

In the present embodiment, it is difficult to provide sharp spectrum characteristics as those of the optical filter in the above-described first embodiment. In such case, an effect similar to that in the first embodiment can be provided if an average light intensity of no less than 20% and no more than 70% for the wavelength range of no less than 460 nm and no more than 500 nm is provided relative to a maximum intensity in the wavelength range of no less than 400 nm and no more than 450 nm as in a fourth LED in FIG. 11.

Third Embodiment

Next, a third embodiment of the present invention will be described.

Figure 12:
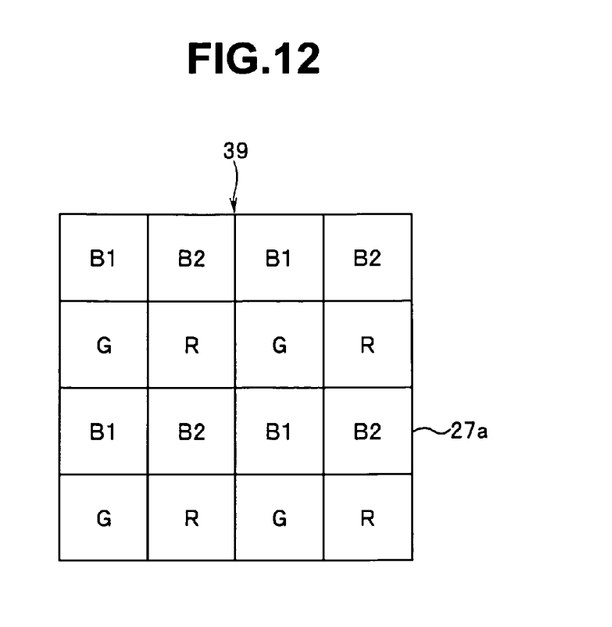
FIG. 12 relates to a third embodiment of the present invention, and is a schematic diagram illustrating a configuration of a light receiving section of a solid image pickup device.
Figure 13:
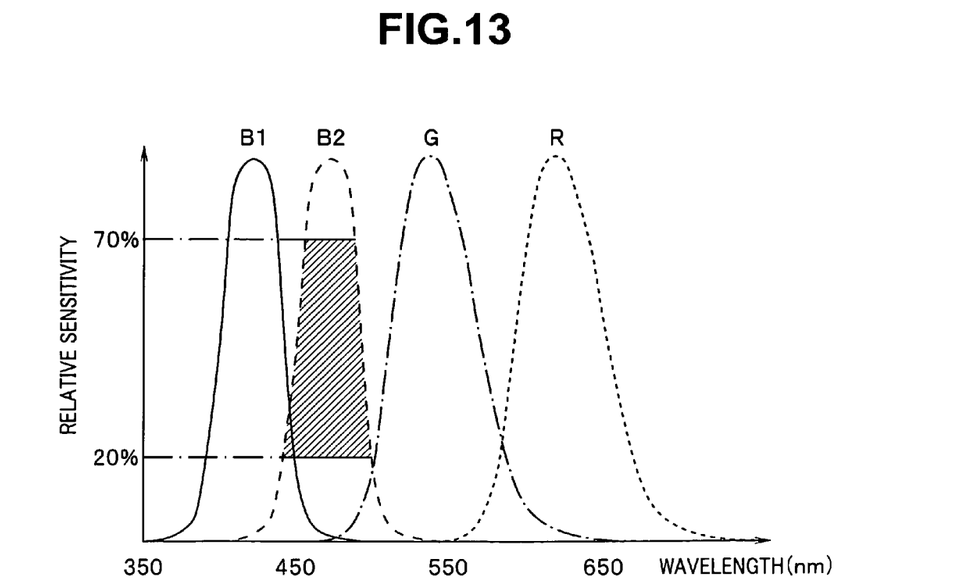
FIG. 13 relates to the third embodiment of the present invention, and is a graph indicating relative sensitivity characteristics of spectra detected by a solid image pickup device.

FIGS. 12 and 13 relate to the third embodiment of the present invention: FIG. 12 is a schematic diagram illustrating a configuration of a light receiving section of a solid image pickup device; and FIG. 13 is a graph indicating a relative sensitivity of a spectrum detected by the solid image pickup device. In the present embodiment, also, components described in the first embodiment will be described using same reference numerals as those of the first embodiment.

As illustrated in FIG. 12, in a solid image pickup device 27 in an image pickup unit 25, a solid image pickup device-on-chip color filter (hereinafter simply referred to as "color filter") 39 in which a blue color B1, a blue color B2, a green color G and a red color R are arranged in a matrix is arranged in a light receiving sensor section 27a.

Here, as indicated in FIG. 13, in the color filter 39, the blue color B1 transmits only light in a wavelength range of around 350 nm (400 nm in visible light) to around 450 nm, the blue color B2 transmits only light in a wavelength range of 450 nm to around 500 nm, the green color G transmits only light in a wavelength range of around 500 nm to around 570 nm, and the red color R transmits only light in a wavelength range of around 570 nm to around 660 nm, and the light transmitted by the respective colors B1, B2, G and R is detected by the light receiving sensor section 27a in the solid image pickup device 27 and loaded as a color image.

Therefore, in the present embodiment, the transmission characteristics of the blue color B2 of the color filter 39 are determined so as to correspond to the wavelength range of around 450 nm to around 500 nm causing deterioration in color contrast of hemoglobin to cell tissues in a body. Then, in the process of performing photoelectric conversion of light passing through the blue color B2 of the color filter 39 by means of the image pickup unit 25, the charge is decreased to between 20% and 70% (the shaded region in FIG. 13), and color-composite image pickup signals are generated.

As described above, the present embodiment is configured to decrease the charge of light in the wavelength range of around 450 nm to around 500 nm detected by the image pickup unit 25 to between 20% and 70%, as opposed to the optical adjustment of transmitted light in the first embodiment.

With such configuration, the endoscope system 1 according to the present embodiment also exerts an effect similar to that provided by the first embodiment, enabling color reproduction in in-vivo observation similar to that in observation under visible light (white color light), and provision of enhanced display of contrast of vessels in a body without causing, e.g., halation, which causes harmful light rays, and thus, enhances expression of vessels, providing an advantage in, for example, facilitating determination of an affected site in which the amount of production of vessels increases.

The invention described in the respective embodiments above is not limited to the embodiments and the variations thereof, and various other variations are possible in practice as long as such other variations do not deviate from the spirit of the present invention.

What is claimed is:

1. A transmittance adjusting device comprising: a transmittance for a wavelength range of no less than 460 nm and no more than 500 nm is set to no less than 20% and no more than 70% relative to a transmittance for a wavelength at a first optical absorption peak of hemoglobin, for white illuminating light from an illuminating light supply section or reflected light from an object illuminated with the illuminating light.

2. An observation apparatus comprising:
    an image pickup section for detecting reflected light from an object in a body, the object being illuminated with white illuminating light, to pick up an image of the object; and
    a transmittance adjusting section in which a transmittance for a wavelength range of no less than 460 nm and no more than 500 nm is set to no less than 20% and no more than 70% relative to a transmittance for a wavelength at a first optical absorption peak of hemoglobin, for the illuminating light or the reflected light.

3. The observation apparatus according to claim 2, wherein the transmittance adjusting section includes a filter disposed on an optical path of the illuminating light or the reflected light.

4. An observation system comprising:
    an illuminating light supply section for supplying illuminating light having a specific wavelength range;
    an image pickup section for detecting reflected light from an object in a body, the object being illuminated with the illuminating light, to pick up an image of the object; and
    a transmittance adjusting section in which a transmittance for a wavelength range of no less than 460 nm and no more than 500 nm t is set to no less than 20% and no more than 70% relative to a transmittance for a wavelength at a first optical absorption peak of hemoglobin, for the illuminating light or the reflected light.

5. The observation system according to claim 4, wherein the transmittance adjusting section includes a filter disposed on an optical path of the illuminating light or the reflected light.

6. A transmittance adjusting device comprising: a transmittance for a wavelength range of no less than 460 nm and no more than 500 nm is set to no less than 20% and no more than 70% relative to a transmittance for a wavelength at a first optical absorption peak of hemoglobin, for white illuminating light from illuminating light supply means or reflected light from an object illuminated with the illuminating light.

7. An observation apparatus comprising:
    image pickup means for detecting reflected light from an object in a body, the object being illuminated with white illuminating light, to pick up an image of the object; and
    transmittance adjusting means in which a transmittance for a wavelength range of no less than 460 nm and no more than 500 nm is set to no less than 20% and no more than 70% relative to a transmittance for a wavelength at a first optical absorption peak of hemoglobin, for the illuminating light or the reflected light.

8. An observation system comprising:
    illuminating light supply means for supplying illuminating light having a specific wavelength range;
    image pickup means for detecting reflected light from an object in a body, the object being illuminated with the illuminating light, to pick up an image of the object; and
    transmittance adjusting means in which a transmittance for a wavelength range of no less than 460 nm and no more than 500 nm is set to no less than 20% and no more than 70% relative to a transmittance for a wavelength at a first optical absorption peak of hemoglobin, for the illuminating light or the reflected light.

* * * * *